US011612521B2

(12) United States Patent
Ishikawa

(10) Patent No.: US 11,612,521 B2
(45) Date of Patent: Mar. 28, 2023

(54) UNDERPANTS-TYPE DISPOSABLE DIAPER

(71) Applicant: Daio Paper Corporation, Ehime (JP)

(72) Inventor: Yoshitake Ishikawa, Ehime (JP)

(73) Assignee: Daio Paper Corporation, Ehime (JP)

( * ) Notice: Subject to any disclaimer, the term of this patent is extended or adjusted under 35 U.S.C. 154(b) by 541 days.

(21) Appl. No.: 16/620,774

(22) PCT Filed: May 11, 2018

(86) PCT No.: PCT/JP2018/018269
§ 371 (c)(1),
(2) Date: Dec. 9, 2019

(87) PCT Pub. No.: WO2018/230216
PCT Pub. Date: Dec. 20, 2018

(65) Prior Publication Data
US 2021/0137750 A1    May 13, 2021

(30) Foreign Application Priority Data

Jun. 16, 2017   (JP) .............................. JP2017-118290

(51) Int. Cl.
A61F 13/49      (2006.01)
A61F 13/496     (2006.01)
A61F 13/514     (2006.01)

(52) U.S. Cl.
CPC ...... A61F 13/49012 (2013.01); A61F 13/496 (2013.01); A61F 13/51474 (2013.01)

(58) Field of Classification Search
CPC .............. A61F 13/49012; A61F 13/496; A61F 13/51474; A61F 13/49011;
(Continued)

(56) References Cited

U.S. PATENT DOCUMENTS 8,282,617 B2 * 10/2012 Kaneda ............. A61F 13/49011
                                                604/385.27
10,064,763 B2 * 9/2018 Takahashi ......... A61F 13/49058
(Continued)

FOREIGN PATENT DOCUMENTS

JP    2005-287930    10/2005
JP    2008-023116    2/2008
(Continued)

OTHER PUBLICATIONS

International Search Report for PCT/JP2018/018269, dated Jun. 5, 2018.

Primary Examiner — Catharine L Anderson
(74) Attorney, Agent, or Firm — Andrus Intellectual Property Law

(57) ABSTRACT

A waist portion W has a first portion P1 and a second portion P2 each including a waist elastic member. The first portion P1 includes an over sheet layer folded back at an edge of a waist opening WO extending to an inside of a waist inner sheet layer. The over sheet layer is formed of a sheet material having a portion folded back at an edge of the waist opening WO from a position outside the waist elastic member in the second portion P2 and extending to a position inside the waist elastic member in the second portion P2. In the first portion P1, the waist elastic member is not fixed to the sheet material. In the second portion P2, the waist elastic member is fixed to the sheet material, and the sheet material is contracted in a width direction WD together with the waist elastic member.

13 Claims, 12 Drawing Sheets

(58) Field of Classification Search
CPC .......... A61F 13/49014; A61F 13/49061; A61F 2013/49025; A61F 2013/49026; A61F 2013/49028
See application file for complete search history.

(56) References Cited

U.S. PATENT DOCUMENTS

| | | | |
|---|---|---|---|
| 11,298,272 B2 * | 4/2022 | Morimoto | ......... A61F 13/49061 |
| 2011/0184372 A1 * | 7/2011 | Esping | .............. A61F 13/49012 |
| | | | 604/392 |

FOREIGN PATENT DOCUMENTS

| | | |
|---|---|---|
| JP | 2008-049013 | 3/2008 |
| JP | 2008-295838 | 12/2008 |
| JP | 2011-254996 | 12/2011 |
| JP | 2014-166242 | 9/2014 |
| JP | 2014-171689 | 9/2014 |
| JP | 2015-171503 | 10/2015 |
| JP | 2014171689 A * | 3/2017 |

* cited by examiner

[FIG.1]
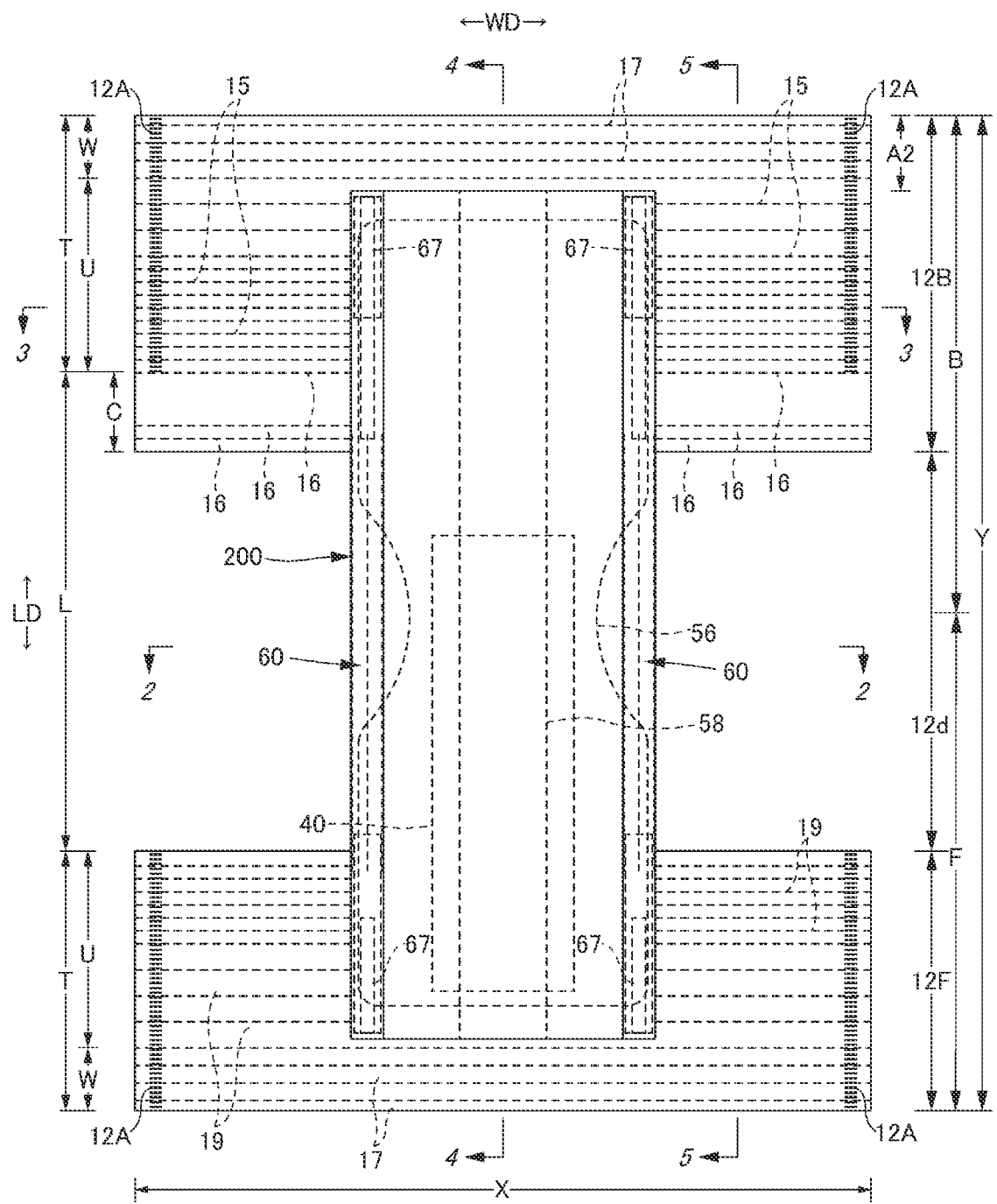

[FIG.2]
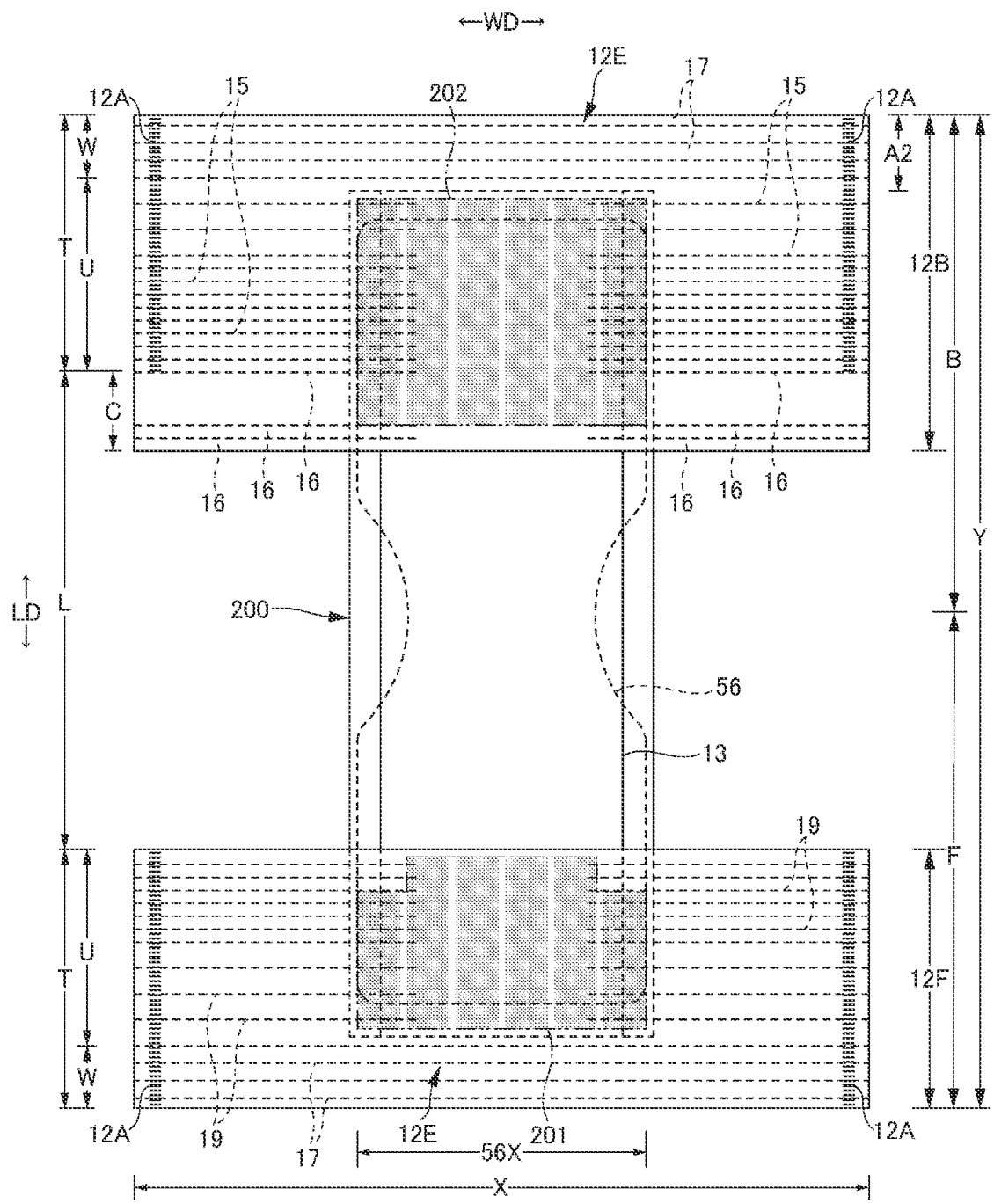

[FIG.3]
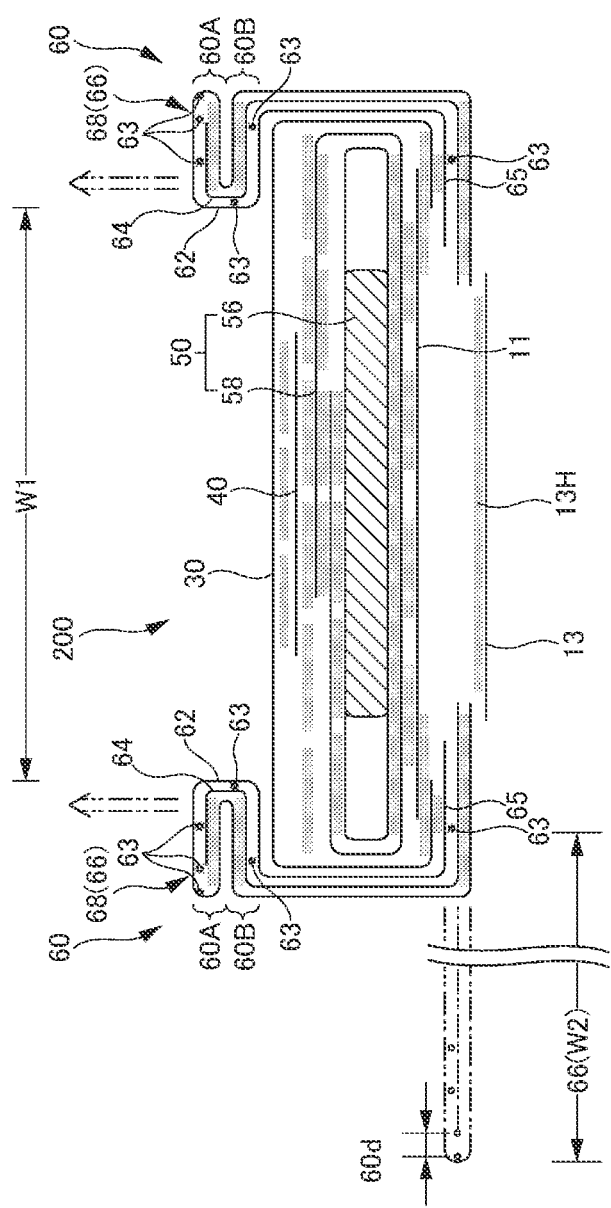

[FIG.4]
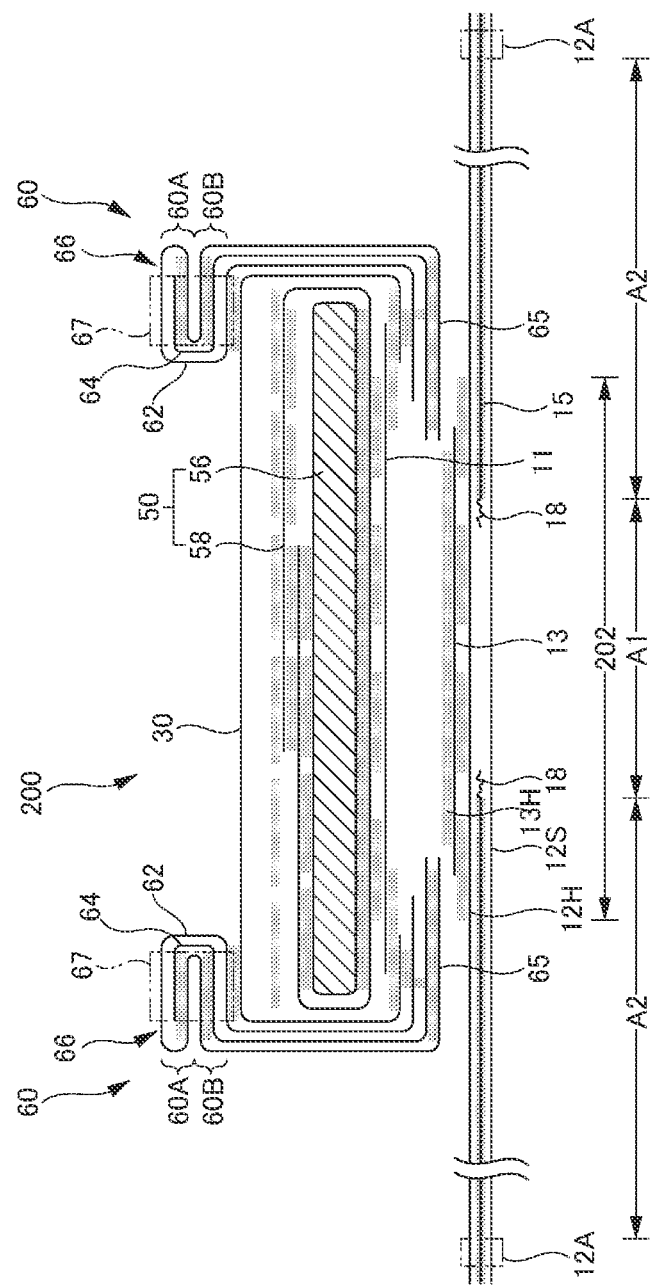

[FIG.5]
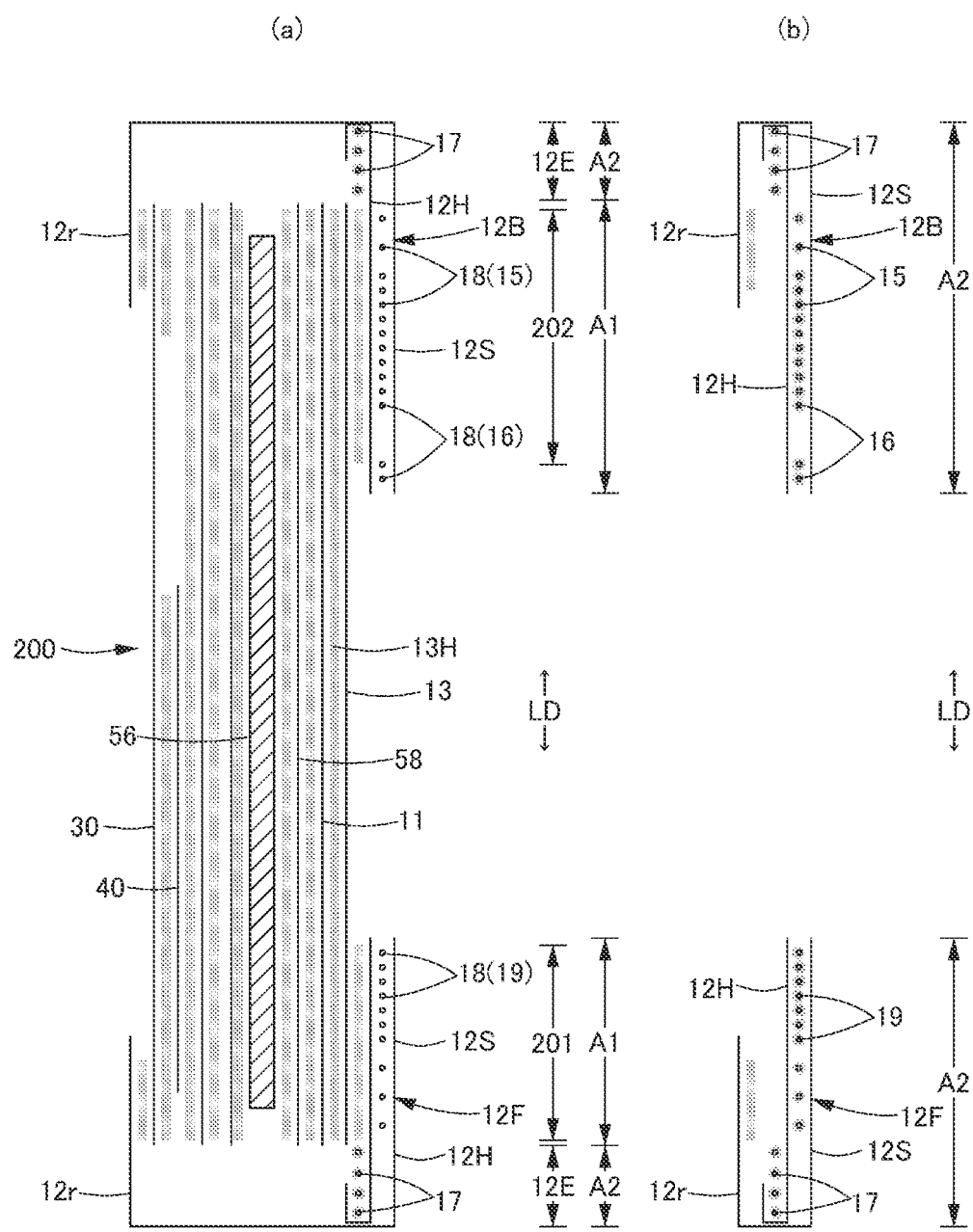

[FIG.6]
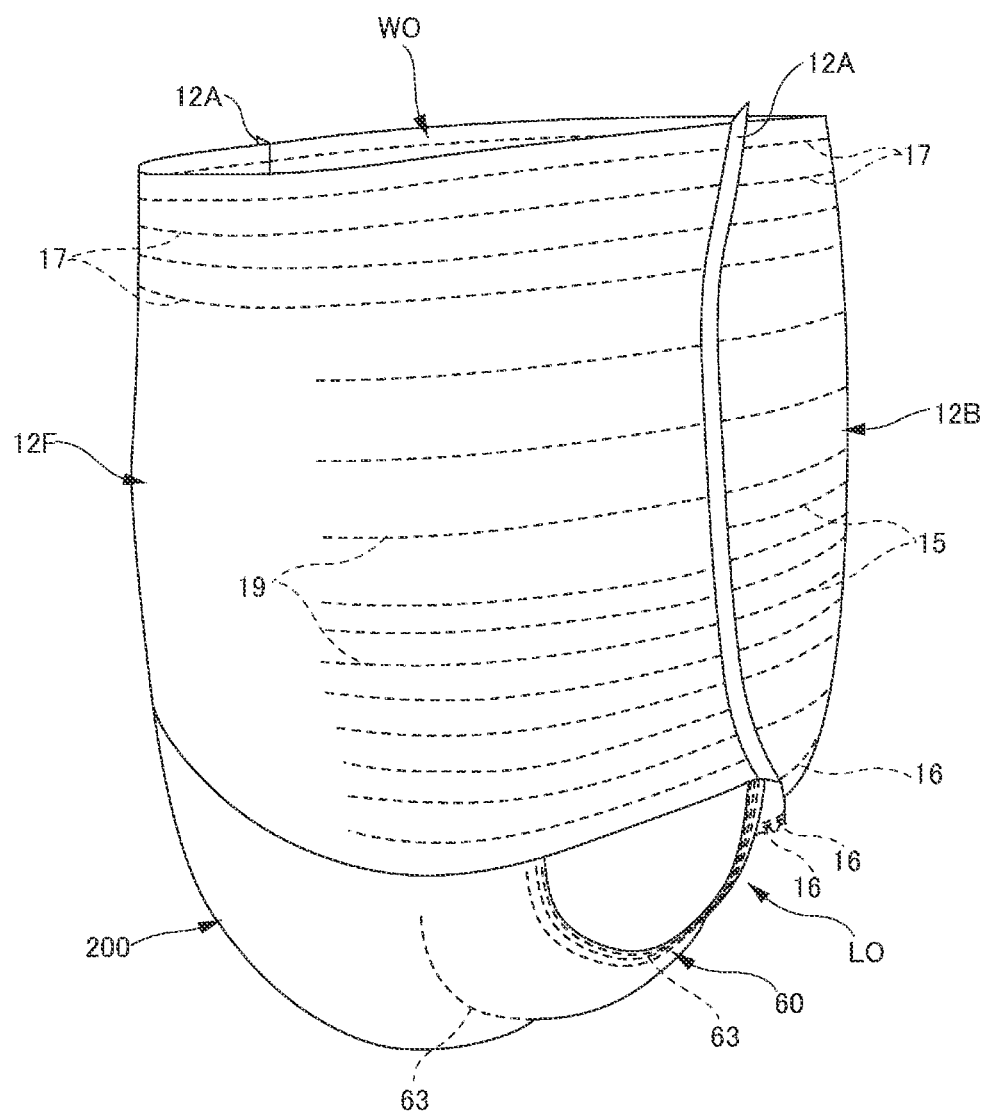

[FIG.7]
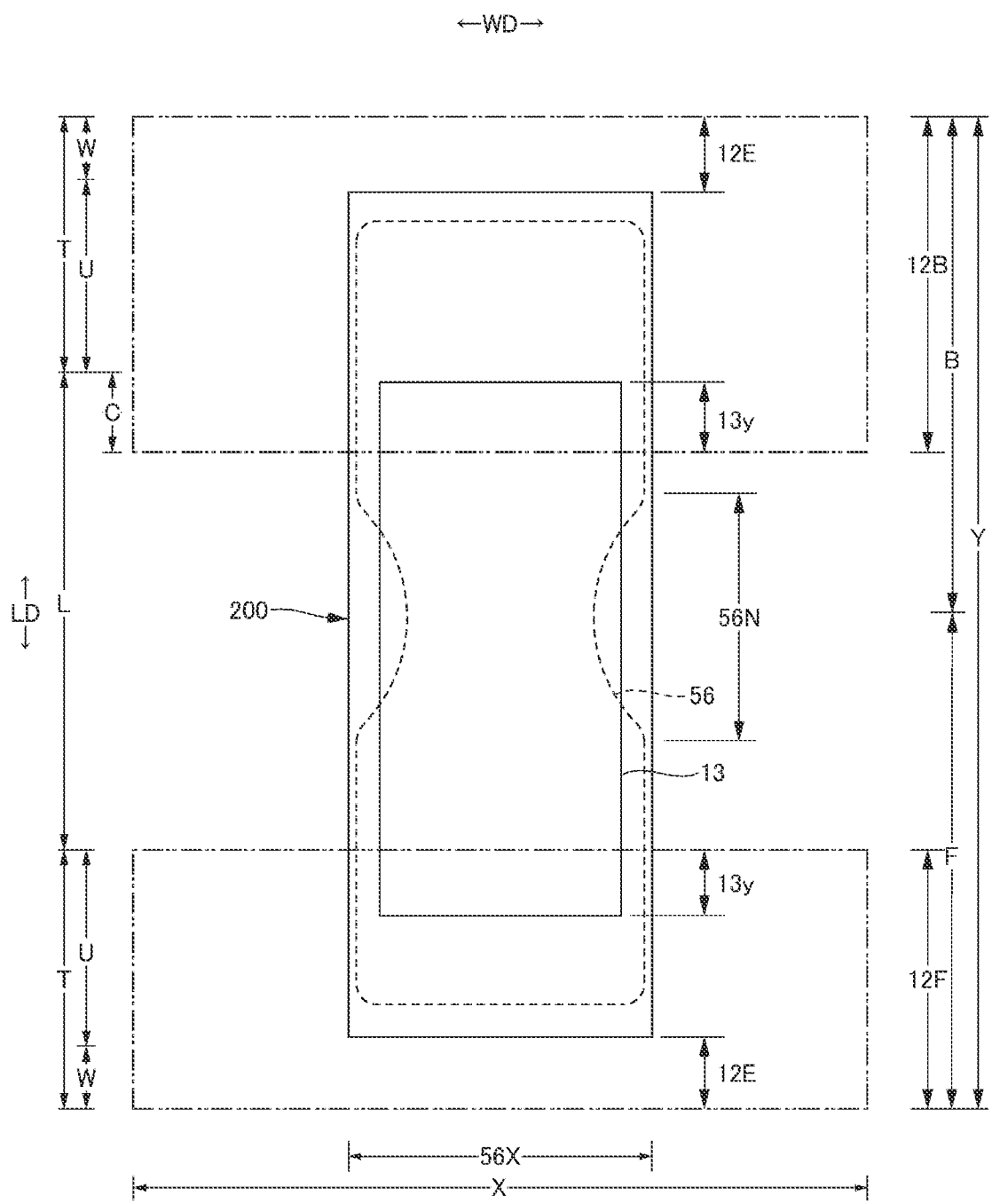

[FIG.8]
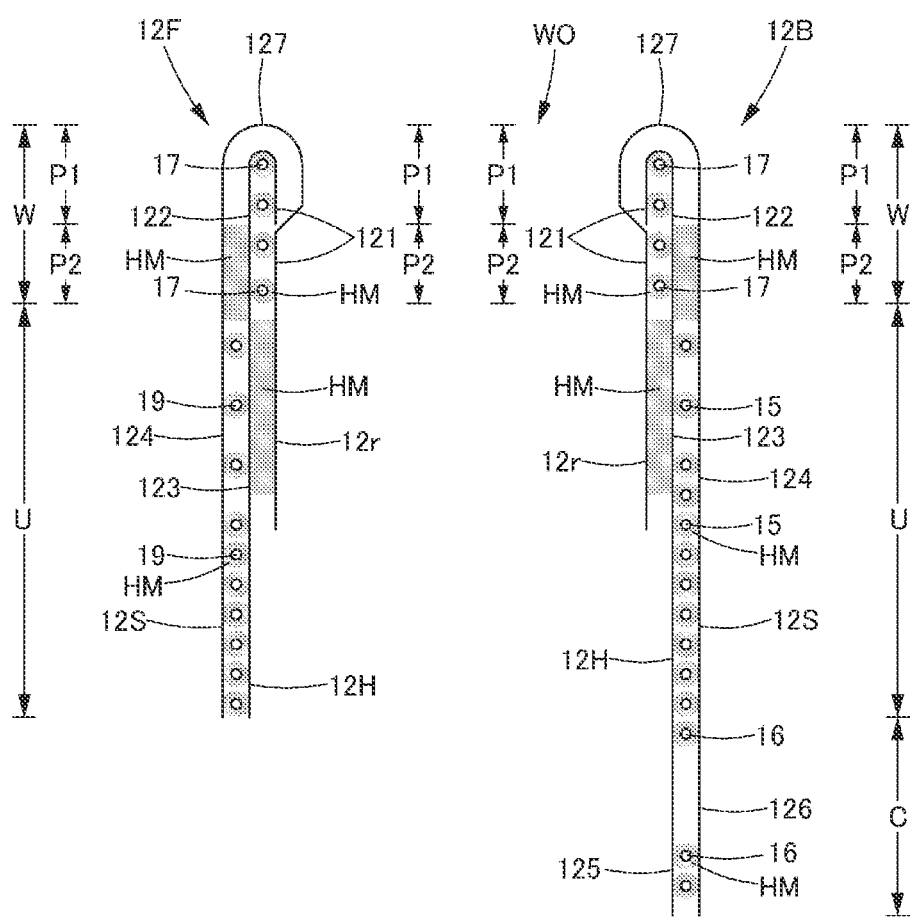

[FIG.9]
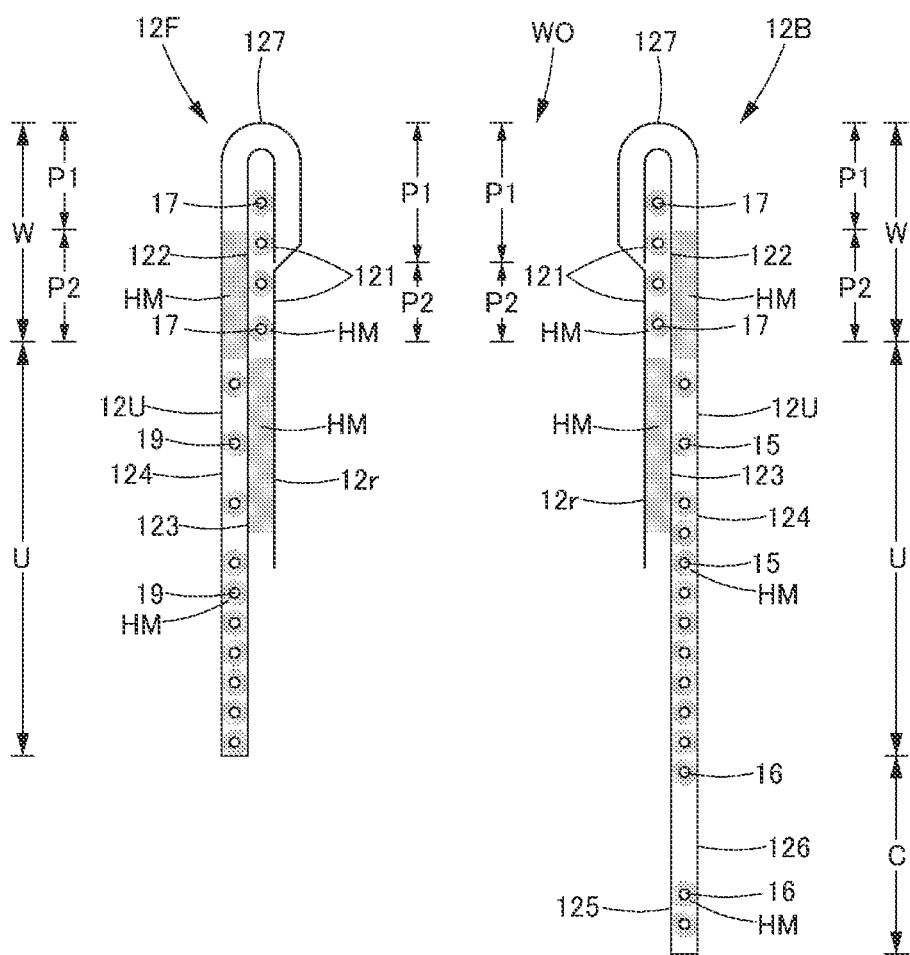

[FIG.10]
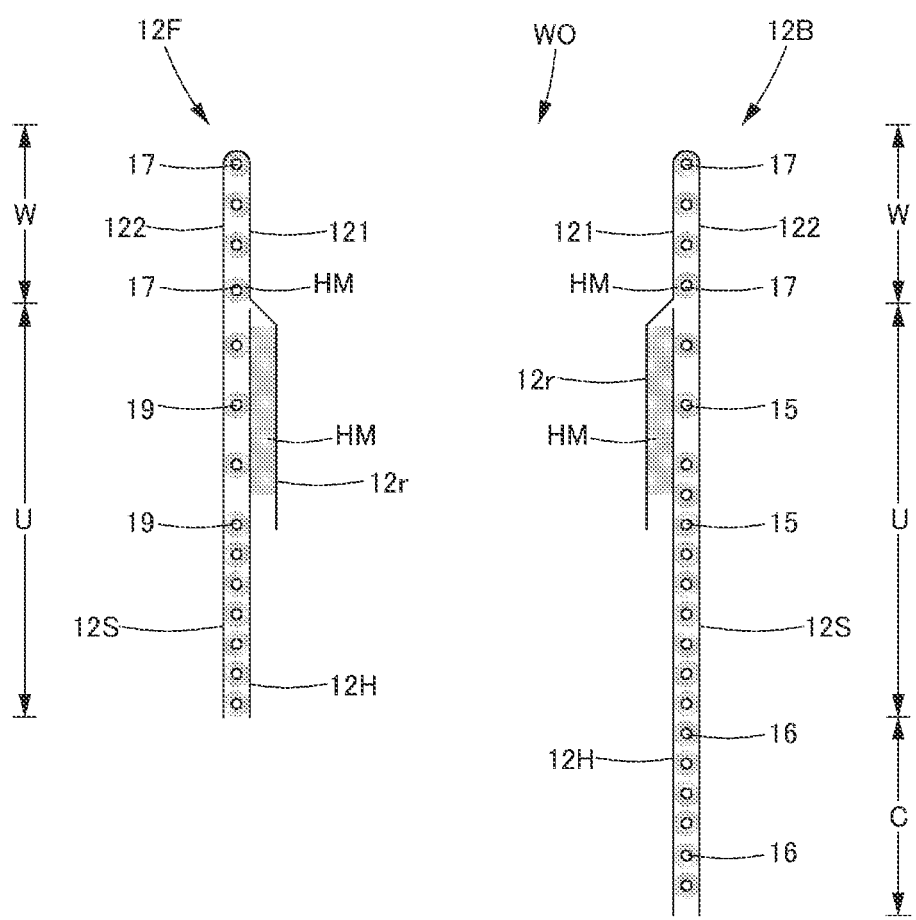

[FIG.11]
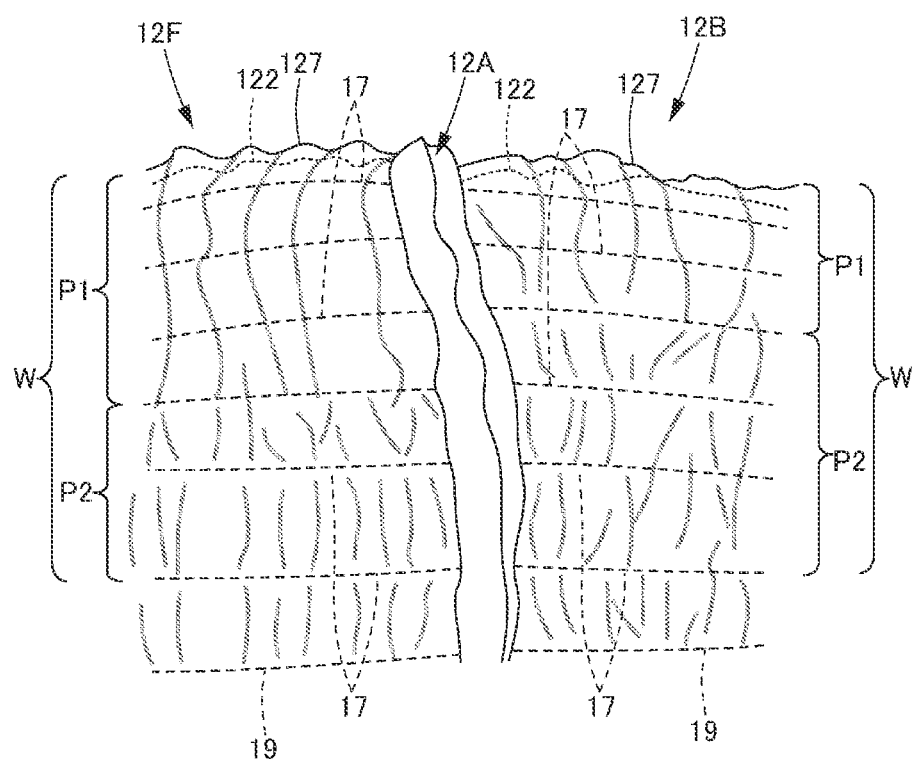

[FIG.12]
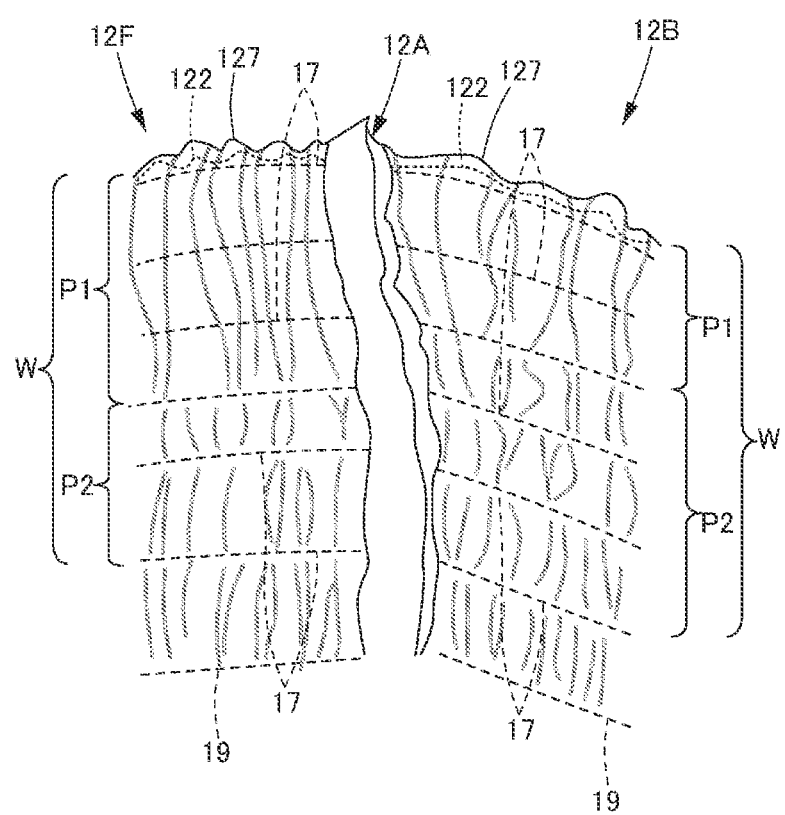

UNDERPANTS-TYPE DISPOSABLE DIAPER

CROSS-REFERENCE TO RELATED APPLICATIONS

This application is the U.S. national stage application of International Application PCT/JP2018/018269, filed May 11, 2018, which international application was published on Dec. 20, 2018, as International Publication WO 2018/230216 in the Japanese language. The International Application claims priority of Japanese Patent Application No. 2017-118290, filed Jun. 16, 2017. The international application and Japanese application are both incorporated herein by reference, in entirety.

TECHNICAL FIELD

The present invention relates to an underpants-type disposable diaper having an improved texture (softness and a cushioning property) at an end portion of a waist opening.

BACKGROUND ART

In general, an underpants-type disposable diaper includes an outer member forming at least lower torso portions of a front body and a back body, and an inner member attached to the outer member so as to extend from the front body to the back body and including an absorber, and has a waist opening and a pair of left and right leg openings formed by bonding both sides of the outer member of the front body to both sides of the outer member of the back body to form a side seal portion (for example, Patent Literatures 1 to 5).

In a general underpants-type disposable diaper, in order to ensure fitting to a body, a region including a waist portion of an outer body has a laminated structure in which an elastic member is interposed between a plurality of sheet layers (see, for example, Patent Literatures 1 to 4).

In such a laminated structure of the outer member, in general, a hot melt adhesive is planarly applied to at least one of an outer sheet layer adjacent to the outer side of the elastic member and an inner sheet layer adjacent to the inner side of the elastic member to bond the outer sheet layer to the inner sheet layer and to fix the elastic member to the outer sheet layer and the inner sheet layer. Alternatively, in order to reduce cost and to improve softness by reducing the amount of use of the hot melt adhesive, the hot melt adhesive is applied to a peripheral surface along a maximum length of the elastic member to bond the outer sheet layer to the inner sheet layer while the elastic member is sandwiched between the outer sheet layer and the inner sheet layer, and the elastic member is fixed to the outer sheet layer and the inner sheet layer.

However, in the conventional underpants-type disposable diaper, there is room for improvement in texture of an end portion of a waist opening when the product is held by hand or worn at the time of wearing or purchasing. More specifically, softness and a cushioning property (compression resilience) of a sheet layer at an edge of a waist opening have an influence on texture of an end portion of the waist opening. However, not only these but also softness and a cushioning property of a corner pressed against a skin when the product is held by hand or worn at the time of wearing or purchasing, that is, softness and a cushioning property of a portion including a waist elastic member closest to the waist opening have a large influence thereon.

Here, as in the conventional example illustrated in FIG. 10, when all of waist elastic members 17 disposed in a waist portion W are fixed to a waist outer sheet layer 122 and a waist inner sheet layer 121 with a hot melt adhesive HM, and at least one of the waist outer sheet layer 122 and the waist inner sheet layer 121 is an outside exposed surface, the waist elastic member 17 closest to the waist opening WO can also touch a skin through only a single sheet layer 121 or 122. Therefore, softness and a cushioning property may be insufficient to impart uncomfortable texture. This point is similar to those described in Patent Literatures 1 to 3.

As described in Patent Literature 4, when the outer sheet layer and the inner sheet layer are not bonded to an end portion of a waist opening and there is a region without a waist elastic member, at softness and a cushioning property at an edge of the waist opening are improved. However, also in this case, all of the waist elastic members are fixed to the outer sheet layer and the inner sheet layer with a hot melt adhesive, and at least one of the outer sheet layer and the inner sheet layer is an outside exposed surface. Therefore, also in this case, when a portion including the elastic member touches a skin, for example, when the waist portion is held by hand or worn, softness and a cushioning property may be insufficient to impart uncomfortable texture.

A diaper described in Patent Literature 5 has an over sheet layer folded back at an edge of a waist opening from a portion closer to a leg opening than a waist portion of an outer sheet layer and extending to a portion closer to the leg opening than a waist portion of an inner sheet layer. The over sheet layer is not bonded to the inner sheet layer or the outer sheet layer over a wide range including the waist portion. Therefore, although fine wrinkles are formed in the outer sheet layer and the inner sheet layer by contraction due to a waist elastic member, wrinkles are hardly formed in the over sheet layer, and only a loose state is obtained. This may be suitable for the purpose of reducing contraction wrinkles as in the diaper described in Patent Literature 5. However, a waist elastic member closest to the waist opening is covered with two sheet layers, but a cushioning property more than the thickness of the sheet is not exhibited. Therefore, there is room for improvement in improving a cushioning property and texture obtained thereby.

CITATION LIST

Patent Literature

Patent Literature 1: JP 2005-287930 A
Patent Literature 2: JP 2008-023116 A
Patent Literature 3: JP 2011-254996 A
Patent Literature 4: JP 2015-171503 A
Patent Literature 5: JP 2008-049013 A

SUMMARY OF INVENTION

Technical Problem

Therefore, a main object of the present invention is to improve texture of an end portion of a waist opening and the like.

Solution to Problem

Typical aspects for solving the above problem are as follows.

First Aspect

An underpants-type disposable diaper including: an outer member forming at least lower torso portions of a front body and a back body; an inner member attached to the outer member so as to extend from the front body to the back body and including an absorber; a waist opening; and a pair of left and right leg openings, a waist portion of the outer member including: a plurality of elongated waist elastic members disposed in a width direction at intervals; a waist inner sheet layer facing insides of the waist elastic members; and a waist outer sheet layer facing outsides of the waist elastic members, the waist elastic members being bonded to the waist inner sheet layer and the waist outer sheet layer via a hot melt adhesive, in which the waist portion has a first portion closer to the waist opening than an intermediate portion in a front-back direction and a second portion opposite thereto, and the first portion and the second portion each have at least one of the waist elastic members, the first portion includes an over sheet layer folded back at an edge of the waist opening from an outside of the waist outer sheet layer and extending to an inside of the waist inner sheet layer, the over sheet layer is formed of a sheet material having a portion folded back at an edge of the waist opening from a position outside the waist elastic member in the second portion and extending to a position inside the waist elastic member in the second portion, in the first portion, the waist elastic member is not fixed to the sheet material, and in the second portion, the waist elastic member is fixed to the sheet material, and the sheet material is contracted in a width direction together with the waist elastic member.

Action and Effect

In the first aspect, the waist inner sheet layer and the waist outer sheet layer are covered with the over sheet layer. Therefore, all the waist elastic members included in the first portion including a waist elastic member closest to the waist opening touch a skin through the two sheet layers.

A portion from an edge of the waist opening to the waist elastic members in the first portion is covered with the over sheet layer released from the waist elastic members, and a free portion of the over sheet layer can be freely deformed with respect to the waist elastic members. Therefore, when the product is held by hand, feel of the waist portion is soft.

Furthermore, in the second portion, a contraction force of the waist elastic members directly act on the sheet material forming the over sheet layer, and the sheet material has firm contraction wrinkles. In the first portion, the sheet material forming the over sheet layer is released from the waist elastic members, but has contraction wrinkles continuous from the second portion due to an influence of the contraction deformation of the second portion. That is, not only the portion from the edge of the waist opening to the waist elastic members of the first portion is covered with the over sheet layer released from the waist elastic members, but also contraction wrinkles are formed in at least the first portion of the over sheet layer. Due to the contraction wrinkles, a cushioning property of a corner pressed against a skin when the product is held by hand or worn at the time of wearing or purchasing, that is, a cushioning property of a portion including a waist elastic member closest to the waist opening increases.

Therefore, according to the present first aspect, texture of an end portion of the waist opening is better than that of a diaper having a conventional over sheet layer.

Second Aspect

The underpants-type disposable diaper according to the first aspect, in which the outer member has an under-waist portion located below the waist portion at the lower torso portion, the under-waist portion of the outer member includes: a plurality of elongated under-waist elastic members disposed in a width direction at intervals; an under-waist inner sheet layer facing insides of the under-waist elastic members; and an under-waist outer sheet layer facing outsides of the under-waist elastic members, the under-waist elastic members are bonded to the under-waist inner sheet layer and the under-waist outer sheet layer via a hot melt adhesive, a first sheet material forming the under-waist outer sheet layer and a second sheet material forming the under-waist inner sheet layer are both folded inward at an edge of the waist opening through the waist portion, the portion folded inward at the edge of the waist opening in the first sheet material extends to a leg opening side more than a waist elastic member closest to the leg opening, the portion folded inward at the edge of the waist opening in the second sheet material extends only to a boundary between the first portion and the second portion, the over sheet layer is formed of the first sheet material, the waist outer sheet layer is formed of the second sheet material, the waist inner sheet layer is formed of the second sheet material in the first portion, and is formed of the first sheet material in the second portion, in the first portion, the waist elastic members are bonded to the second sheet material via a hot melt adhesive, and the first sheet material is not bonded to the second sheet material, and in the second portion, the waist elastic members are bonded to the first sheet material facing insides of the waist elastic members via a hot melt adhesive, the waist elastic members are bonded to the second sheet material facing outsides of the waist elastic members via a hot melt adhesive, and the first sheet material is bonded to the second sheet material via a hot melt adhesive.

Action and Effect

According to the present second aspect, the configuration of the sheet material is simple, and manufacture is easy. Therefore, this is preferable.

Third Aspect

The underpants-type disposable diaper according to the second aspect, in which four to ten of the waist elastic members are disposed at intervals of 3 to 7 mm in the front-back direction, and a boundary between the first portion and the second portion is located within a range from a position of a waist elastic member first from the waist opening to a position of a waist elastic member fifth from the waist opening.

Action and Effect

The interval between the waist elastic members and the number thereof are preferably within the above range. In this case, when the boundary between the first portion and the second portion is within the above range, improvement of softness by release of the over sheet layer in the first portion and improvement of a cushioning property by formation of contraction wrinkles are easily achieved at the same time.

Fourth Aspect

The underpants-type disposable diaper according to the second or third aspect, in which an interval between the edge of the waist opening and the waist elastic member closest to the waist opening in the front-back direction is 5 mm or less.

Action and Effect

When the interval between the edge of the waist opening and the waist elastic member closest to the waist opening in a front-back direction is 5 mm or less, contraction wrinkles formed in the first portion by contraction of the second portion are formed nicely to the edge of the waist opening or in the vicinity thereof, and therefore this is preferable.

Fifth Aspect

The underpants-type disposable diaper according to any one of the second to fourth aspects, in which a surface of the first sheet material facing the second sheet material and a surface of the second sheet material facing the first sheet material each have an average surface friction coefficient MIU of 0.30 or less.

Action and Effect

When the first sheet material and the second sheet material are slippery materials, the over sheet layer is slippery with respect to the waist inner sheet layer and the waist outer sheet layer, and resistance during deformation of the free portion of the over sheet layer is reduced. Therefore, softness of the portion having the over sheet layer is further improved.

Sixth Aspect

The underpants-type disposable diaper according to any one of first to fifth aspects, in which a boundary between the first portion and the second portion outside the waist portion is closer to the waist opening than a boundary between the first portion and the second portion inside the waist portion.

Action and Effect

With such a configuration as in the present aspect, the appearance of the waist portion does not give a loose impression while texture of an end portion of a waist opening felt by a wearer is good, and therefore this is preferable.

Advantageous Effects of Invention

As described above, according to the present invention, texture at an end portion of a waist opening is improved advantageously, for example.

BRIEF DESCRIPTION OF DRAWINGS

FIG. 1 is a plan view illustrating an inner surface of an underpants-type disposable diaper in an unfolded state.

FIG. 2 is a plan view illustrating an outer surface of the underpants-type disposable diaper in an unfolded state.

FIG. 3 is a cross-sectional view cut along 2-2 of FIG. 1.

FIG. 4 is a cross-sectional view cut along 3-3 of FIG. 1.

FIG. 5($a$) is a cross-sectional view cut along 4-4 of FIG. 1, and FIG. 5($b$) is a cross-sectional view cut along 5-5 of FIG. 1.

FIG. 6 is a perspective view of the underpants-type disposable diaper.

FIG. 7 is a plan view illustrating an outer surface of an inner member in an unfolded state together with an outline of an outer member.

FIG. 8 is a cross-sectional view of a front outer member and a back outer member.

FIG. 9 is a cross-sectional view of a front outer member and a back outer member.

FIG. 10 is a cross-sectional view of a front outer member and a back outer member.

FIG. 11 is a side view illustrating a main part of a trial underpants-type disposable diaper in a wearing state.

FIG. 12 is a side view illustrating a main part of a trial underpants-type disposable diaper in a natural length state.

DESCRIPTION OF EMBODIMENTS

Hereinafter, an embodiment of the present invention will be described in detail with reference to the attached drawings. A dotted pattern portion in the cross-sectional views illustrates an adhesive as a bonding means for bonding constituent members located on a front surface side and a back surface side, and is formed by applying a hot melt adhesive by solid application, bead application, curtain application, summit application, spiral application, pattern coating (transfer of a hot melt adhesive by a letterpress method), or the like. A fixing portion of an elastic member is formed, instead of this or in addition to this, by application to an outer peripheral surface of an elastic member by a comb gun, SureWrap application, or the like. Examples of the hot melt adhesive include an EVA-based agent, a pressure-sensitive rubber-based agent (elastomer-based agent), an olefin-based agent, and a polyester/polyamide-based agent, and these can be used without particular limitation. As a bonding means for bonding constituent members, a means by material welding such as heat sealing or ultrasonic sealing can also be used.

FIGS. 1 to 6 illustrate an example of an underpants-type disposable diaper. The underpants-type disposable diaper includes: a rectangular front outer member 12F forming at least a lower torso portion of a front body F; a rectangular back outer member 12B forming at least a lower torso portion of a back body B; and an inner member 200 disposed inside the outer members 12F and 12B so as to extend from the front outer member 12F to the back outer member 12B through a crotch portion. Both sides of the front outer member 12F and both sides of the back outer member 12B are bonded to each other to form a side seal portion 12A. As a result, an opening formed by the front and back end portions of the outer members 12F and 12B is a waist opening WO through which a wearer's torso passes, and a portion surrounded by lower edges of the outer members 12F and 12B and a side edge of the inner member 200 on both sides of the inner member 200 in the width direction is a leg opening LO through which a leg passes. The inner member 200 is a portion for absorbing and holding excrement such as urine, and the outer members 12F and 12B are portions for supporting the inner member 200 with respect to the body of a wearer. A reference numeral Y represents the maximum length of the diaper in an unfolded state (front-back direction length from an edge of a waist opening WO of the front body F to an edge of a waist opening WO of the back body B), and a reference numeral X represents the maximum width of the diaper in an unfolded state.

The underpants-type disposable diaper in the present form has a lower torso region T defined as a front-back direction range (front-back direction range from the waist opening WO to an upper end of the leg opening LO) having the side seal portion 12A, and an intermediate region L defined as a front-back direction range of a portion forming the leg opening LO (between a front-back direction region having the side seal portion 12A of the front body F and a front-back direction region having the side seal portion 12A of the back body B). The lower torso region T can be divided into a "waist portion" W conceptually forming an edge of the waist opening and an "under-waist portion" U which is a portion lower than the waist portion W. Usually, in a case where the lower torso region T has a boundary in which a stretching stress in a width direction WD changes (for example, the fineness of an elastic member or the stretch rate thereof changes), a portion closer to the waist opening WO than the boundary closest to the waist opening WO is the waist portion W. In a case where there is no such a boundary, a waist extended portion 12E extending so as to be closer to the waist opening WO than the absorber 56 or the inner member 200 is the waist portion W. The front-back direction length varies depending on the size of a product and can be appropriately determined. For example, the length of the waist portion W can be 15 to 40 mm, and the length of the under-waist portion U can be 65 to 120 mm. Meanwhile, both side edges of the intermediate region L are each narrowed in a substantially U shape or a curved shape so as to follow a periphery of a wearer's leg, and the wearer's leg passes therethrough. As a result, the underpants-type disposable diaper in an unfolded state has an approximately hourglass shape as a whole.

Inner Member

The inner member 200 can adopt an arbitrary shape, but is rectangular in the illustrated form. As illustrated in FIGS. 3 to 5, the inner member 200 includes a top sheet 30 located on a body side, a liquid impervious sheet 11, and an absorbent element 50 interposed therebetween, and is a main unit portion having an absorption function. A reference numeral 40 represents an intermediate sheet (second sheet) disposed between the top sheet 30 and the absorbent element 50 in order to rapidly transfer a liquid that has passed through the top sheet 30 to the absorbent element 50. A reference numeral 60 represents a side gather 60 extending so as to come into contact with a periphery of a wearer's leg from both sides of the inner member 200 in order to prevent leakage of excrement into both sides of the inner member 200.

Top Sheet

The top sheet 30 transmits a liquid, and examples thereof include a perforated or imperforated nonwoven fabric and a porous plastic sheet. Among these materials, the nonwoven fabric is not particularly limited concerning a raw material fiber thereof. Examples thereof include a synthetic fiber such as an olefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. For example, if softness and drapeability are demanded, a spunbonding method and a spunlacing method are preferable processing methods. If bulkiness and softness are demanded, an air through method, a point bond method, and a thermal bond method are preferable processing methods.

The top sheet 30 may be formed of a single sheet or a laminated sheet obtained by sticking two or more sheets to each other. Similarly, the top sheet 30 may be formed of a single sheet or two or more sheets in a plane direction.

Both sides of the top sheet 30 may be folded back to a back surface side at a side edge of the absorbent element 50 or may protrude from the side edge of the absorbent element 50 to a lateral side without being folded back.

For the purpose of preventing positional deviation with respect to a back surface side member or the like, it is desirable that the top sheet 30 is fixed to a member adjacent to the back surface side by a bonding means by material welding such as heat sealing or ultrasonic sealing, or with a hot melt adhesive. In the illustrated example, the top sheet 30 is fixed to a surface of an intermediate sheet 40 and a surface of a portion located on a front surface side of the absorber 56 in a wrapping sheet 58 with a hot melt adhesive applied to a back surface thereof.

Intermediate Sheet

In order to quickly transfer a liquid that has passed through the top sheet 30 to the absorber, it is possible to dispose the intermediate sheet (also referred to as "second sheet") 40 having a higher liquid transmission rate than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, point bonded nonwoven fabric, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 $g/m^2$, and more preferably 25 to 60 $g/m^2$. A raw material fiber of the nonwoven fabric preferably has a fineness of 2.0 to 10 dtex. In order to make the nonwoven fabric bulky, as mixed fibers of all or some of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. The front-back direction length of the intermediate sheet 40 may be the same as the maximum length of the diaper, may be the same as the length of the absorbent element 50, or may be within a short length range centered on a liquid receiving region.

For the purpose of preventing positional deviation with respect to a back surface side member or the like, it is desirable that the intermediate sheet 40 is fixed to a member adjacent to the back surface side by a bonding means by material welding such as heat sealing or ultrasonic sealing, or with a hot melt adhesive. In the illustrated example, the intermediate sheet 40 is fixed to a surface of a portion located on a front surface side of the absorber 56 in the wrapping sheet 58 with a hot melt adhesive applied to a back surface thereof.

Liquid Impervious Sheet

A material of the liquid impervious sheet 11 is not particularly limited, but examples thereof include a plastic film formed of an olefin-based resin such as polyethylene or polypropylene, a laminated nonwoven fabric having a plastic film disposed on a surface of a nonwoven fabric, and a laminated sheet obtained by superposing and bonding a nonwoven fabric or the like to a plastic film. For the liquid impervious sheet 11, it is preferable to use a liquid impervious and moisture pervious material favorably used from a viewpoint of preventing stuffiness. As a moisture pervious plastic film, a microporous plastic film obtained by kneading an inorganic filler in an olefin-based resin such as polyethylene or polypropylene, molding a sheet, and then stretching the sheet in a monoaxial or biaxial direction is widely used. In addition, a nonwoven fabric using a micro denier fiber, a nonwoven fabric that has reinforced leakproofness by reducing a space between fibers by applying heat and pressure, and a sheet that has become liquid impervious without using a plastic film by a method for applying a super absorbent polymer, a hydrophobic resin, or a water repellent agent can be used as the liquid impervious sheet 11. However, it is desirable to use a resin film in order to obtain sufficient bonding strength at the time of bonding to a cover nonwoven fabric 13 described later through a hot melt adhesive.

The liquid impervious sheet 11 may have a width housed in a back surface side of the absorbent element 50 as illustrated in the drawing, or may go around both sides of the absorbent element 50 and extend to both sides of a side surface of the top sheet 30 of the absorbent element 50 in order to enhance leakproofness. The extending portion appropriately has a width of about 5 to 20 mm on each of the left and the right.

On an inner side of the liquid impervious sheet 11, in particular, on a side surface of the absorber 56, an excretion indicator that changes a color due to absorption of a liquid can be disposed.

Side Gather

The side gather 60 extends along both sides of the inner member 200 over the entire front-back direction LD and is disposed in order to prevent side leakage by being in contact with the periphery of a wearer's leg, and includes what is generally called a three-dimensional dimensional gather or a plane gather.

The side gather 60 illustrated in FIGS. 1, 3, and 4 is a so-called three-dimensional gather, and rises from a side of the inner member 200 to a front surface side. In the side gather 60, a root side portion 60B rises obliquely toward the center in the width direction, and a tip side portion 60A of the intermediate portion rises obliquely outward in the width direction. However, the side gather 60 is not limited thereto, and can be changed appropriately. For example, the side gather 60 can rise toward the center in the width direction as a whole.

More specifically, the side gather 60 in the illustrated example is formed by folding back a belt-shaped gather nonwoven fabric 62 having a length equal to the front-back direction length of the inner member 200 in the width direction WD at a tip portion to be folded in two, and fixing a plurality of elongated gather elastic members 63 to the folded portion and between the sheets near the folded portion in a stretched state in a longitudinal direction at intervals in the width direction WD. A base portion of the side gather 60 opposite to a tip portion thereof (an end portion opposite to the sheet-folded portion in the width direction WD) is a root portion 65 fixed to a side of a back surface side of the liquid impervious sheet 11 in the inner member 200, and a portion other than the root portion 65 is a main unit portion 66 (portion on the folded portion side) extending from the root portion 65. The main unit portion 66 has the root side portion 60B extending toward the center in the width direction, and the tip side portion 60A folded back at a tip of the root side portion 60B and extending outward in the width direction. In this form, the surface contact type side gather 60 is adopted. However, a line contact type side gather 60 not folded back outward in the width direction can also be adopted. Front-back direction both end portions of the main unit portion 66 are fallen portions 67 fixed to a side surface of the top sheet 30 in a state of falling down. Meanwhile, a front-back direction intermediate portion located therebetween is a non-fixed free portion 68. The gather elastic member 63 in the front-back direction LD is fixed in a stretched state at least to a tip portion of the free portion 68.

In the side gather 60 configured as described above, a contraction force of the gather elastic member 63 acts so as to bring the front-back direction both end portions closer to each other. However, the front-back direction both end portions of the main unit portion 66 are fixed so as not to rise, whereas a portion therebetween is the non-fixed free portion 68. Therefore, only the free portion 68 rises so as to come into contact with a body side as illustrated by the arrow in FIG. 3. In particular, when the root portion 65 is located on a back surface side of the inner member 200, the free portion 68 rises so as to open outward in the width direction at a crotch portion and in the vicinity thereof. Therefore, the side gather 60 comes into contact with a periphery of a leg with a surface to improve fitting.

Like the side gather 60 in the illustrated example, in a bent form in which the main unit portion 66 includes the root side portion 60B extending toward the center in the width direction and the tip side portion 60A folded back at a tip of the root side portion 60B and extending outward in the width direction, the tip side portion 60A is bonded to the root side portion 60B in a state of falling down at the fallen portion 67, and the root side portion 60B is bonded to the top sheet 30 in a state of falling down. For bonding facing surfaces to each other in the fallen portion 67, at least one of a hot melt adhesive by various application methods and a means by material welding such as heat sealing or ultrasonic sealing can be used. In this case, bonding of the root side portion 60B to the top sheet 30 and bonding of the tip side portion 60A to the root side portion 60B may be performed by the same means or by different means. For example, it is one preferable form to bond the root side portion 60B to the top sheet 30 with a hot melt adhesive, and to bond the tip side portion 60A to the root side portion 60B by material welding.

As the gather nonwoven fabric 62, a product obtained by subjecting a soft nonwoven fabric having excellent uniformity and concealability, such as a spunbonded nonwoven fabric (SS, SSS, or the like), an SMS nonwoven fabric (SMS, SSMMS, or the like), or a melt blown nonwoven fabric, to a water repellent treatment with silicon or the like as necessary can be used suitably. The gather nonwoven fabric 62 preferably has a fiber basis weight of about 10 to 30 g/m$^2$. As the gather elastic member 63, a rubber thread or the like can be used. When a spandex rubber thread is used, the spandex rubber thread preferably has a fineness of 470 to 1240 dtex, more preferably 620 to 940 dtex. The rubber thread preferably has a stretch rate of 150 to 350%, more preferably 200 to 300% at the time of fixing. Note that the term "stretch rate" means a value obtained when a natural length is assumed to be 100%. As illustrated in the drawing, a waterproof film 64 can be interposed between the two portions obtained by folding the gather nonwoven fabric 62, and in this case, the gather nonwoven fabric 62 can be partially omitted in a portion where the waterproof film 64 is present. However, in order to impart a cloth-like appearance and a cloth-like texture to a product, at least an outer surface from a base end of the side gather 60 to a tip thereof needs to be formed of the gather nonwoven fabric 62 as in the illustrated example.

The number of the gather elastic members 63 disposed in the free portion of the side gather 60 is preferably two to six, and more preferably three to five. A disposition interval 60*d* is suitably 3 to 10 mm. With such a configuration, a range where the gather elastic member 63 is disposed easily comes into contact with a skin with a surface. The gather elastic member 63 may be disposed not only on a tip side but also on a root side.

In the free portion 68 of the side gather 60, for sticking an inner layer and an outer layer of the gather nonwoven fabric 62 to each other or fixing the gather elastic member 63 sandwiched therebetween, at least one of a hot melt adhesive by various application methods and a fixing means by material welding such as heat sealing or ultrasonic sealing can be used. When the entire surfaces of the inner layer and the outer layer of the gather nonwoven fabric 62 are stuck to each other, softness is impaired. Therefore, preferably, a portion other than a bonded portion of the gather elastic member 63 is not bonded or weakly bonded. In the illustrated example, by applying a hot melt adhesive only to an outer peripheral surface of the gather elastic member 63 by an application means such as a comb gun or a SureWrap nozzle, and sandwiching the gather elastic member 63 between the inner layer and the outer layer of the gather nonwoven fabric 62, the gather elastic member 63 is fixed to the inner layer and the outer layer of the gather nonwoven fabric 62, and the inner layer and the outer layer of the gather nonwoven fabric 62 are fixed to each other only with the hot melt adhesive applied to the outer peripheral surface of the gather elastic member 63.

Similarly, for fixing the waterproof film 64 incorporated in the side gather 60 to the gather nonwoven fabric 62 and fixing the fallen portion 67, at least one of a hot melt adhesive by various application methods and a means by material welding such as heat sealing or ultrasonic sealing can be used.

The size of the side gather 60 in the illustrated example can be appropriately determined. However, in a case of a baby disposable diaper, for example, as illustrated in FIG. 3, a rising height of the side gather 60 (width direction length of the main unit portion 66 in an unfolded state) W2 is preferably 15 to 60 mm, and particularly preferably 20 to 40 mm. A separation distance W1 between innermost folded portions in a flatly folded state is preferably 60 to 190 mm, and particularly preferably 70 to 140 mm such that the side gather 60 is parallel to a surface of the top sheet 30.

Absorbent Element

The absorbent element 50 includes the absorber 56 and the wrapping sheet 58 wrapping the entire absorber 56. The wrapping sheet 58 can also be omitted.

Absorber

The absorber 56 can be formed by an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 g/m$^2$. In a case of a filament assembly, a fiber basis weight may be, for example, about 30 to 120 g/m$^2$. In a case of a synthetic fiber, a fineness is, for example, 1 to 16 dtex, preferably 1 to 10 dtex, and more preferably 1 to 5 dtex. In a case of a filament assembly, the filament may be formed of non-crimped fibers but is preferably formed of crimped fibers. The degree of crimp of the crimped fibers may be, for example, about 5 to 75, preferably 10 to 50, and more preferably 15 to 50 per 2.54 cm. A uniformly crimped fiber is often used. In the absorber 56, super absorbent polymer particles are preferably dispersed and held.

The absorber 56 may have a rectangular shape. However, as illustrated in FIG. 7 and the like, the absorber 56 preferably has an hourglass shape having a narrower portion 56N with a narrower width than front-back direction both sides thereof in a front-back direction intermediate portion because fitting of the absorber 56 itself and the side gather 60 to a periphery of a leg is improved.

The size of the absorber 56 can be determined appropriately as long as the absorber 56 extends to the front, back, left, and right of a ureteral port position. However, the absorber 56 preferably extends to peripheral edges of the inner member 200 or the vicinity thereof in the front-back direction LD and the width direction WD. Note that a reference numeral 56X represents the maximum width of the absorber 56.

Super Absorbent Polymer Particles

The absorber 56 may contain super absorbent polymer particles partially or entirely. The super absorbent polymer particles include "powder" in addition to "particles". As super absorbent polymer particles 54, those used for this type of disposable diaper can be used as they are. For example, when sieving using a standard sieve of 500 μm (JIS Z8801-1: 2006) (shake for five minutes) is performed, particles in which a ratio of particles remaining on the sieve is 30% by weight or less are desirable. When sieving using a standard sieve of 180 μm (JIS Z8801-1: 2006) (shake for five minutes) is performed, particles in which a ratio of particles remaining on the sieve is 60% by weight or more are desirable.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m² although this cannot be applied generally. The basis weight of a polymer of less than 50 g/m² makes it difficult to secure the absorption amount. The basis weight of more than 350 g/m² saturates an effect.

The spray density or the spray amount of the super absorbent polymer particles in a planar direction of the absorber 56 can be adjusted if necessary. For example, the spray amount at a liquid excretion site can be larger than that at another site. When a gender difference is considered, the spray density (amount) at a front side can be increased for men, and the spray density (amount) at a central portion can be increased for women. It is also possible to locally dispose a portion where no polymer is present (for example, in a spot shape) in a planar direction of the absorber 56.

Wrapping Sheet

In a case where the wrapping sheet 58 is used, as a material thereof, tissue paper, particularly, crepe paper, a nonwoven fabric, a polylaminated nonwoven fabric, a sheet with small holes, and the like can be used. However, it is desirable that the wrapping sheet 58 is a sheet from which super absorbent polymer particles do not escape. In a case where a nonwoven fabric is used instead of crepe paper, a hydrophilic SMS nonwoven fabric (SMS, SSMMS, or the like) is particularly suitable, and polypropylene, a polyethylene/polypropylene composite material, or the like can be used as a material thereof. A nonwoven fabric having a basis weight of 5 to 40 g/m², particularly of 10 to 30 g/m² is desirable.

A wrapping mode of the wrapping sheet 58 can be determined appropriately. However, a form is preferable in which the wrapping sheet 58 is wound around the absorber 56 cylindrically so as to surround front and back surfaces and both side surfaces of the absorber 56, the front and back end portions of the wrapping sheet 58 are caused to protrude from the front and back of the absorber 56, and a wound and overlapping portion and an overlapping portion of the front and back protruding portions are bonded with a hot melt adhesive or by a bonding means such as material welding from viewpoints of ease of manufacture, prevention of leakage of the super absorbent polymer particles from front and back edges, and the like.

Outer Member

The outer members 12F and 12B are formed by the rectangular front outer member 12F forming at least a lower torso portion of the front body F and the rectangular back outer member 12B forming at least a lower torso portion of the back body B, respectively. The front outer member 12F and the back outer member 12B are not continuous on a crotch side, and are separated from each other in the front-back direction LD. A separation distance thereof 12d can be about 150 to 250 mm, for example. The outer members 12F and 12B may be an integral outer member passing a crotch and continuous from the front body F to the back body B as described in Patent Literature 4.

The outer members 12F and 12B each have a lower torso portion which is a front-back direction range corresponding to the lower torso region T. In the present form, the front-back direction size of the back outer member 12B is longer than that of the front outer member 12F, and the front outer member 12F does not have a portion corresponding to the intermediate region L, but the back outer member 12B has a gluteal cover portion C extending from the lower torso region T toward the intermediate region L. Although not illustrated, also in the front outer member 12F, an inguinal cover portion extending from the lower torso region T toward the intermediate region L may be disposed, or the inguinal cover portion may be disposed without a gluteal cover portion. Alternatively, in both the front outer member 12F and the back outer member 12B, it is not necessary to dispose a portion corresponding to the intermediate region L.

The outer members 12F and 12B each include the elastic members 15 to 19 in order to enhance fitting of a wearer to a lower torso, and a stretchable region A2 that elastically stretches and contracts in the width direction WD along with stretching and contracting of the elastic members is formed. In the stretchable region A2, in a natural length state, the outer members 12F and 12B contract along with contraction of an elastic member to form wrinkles or pleats. When the elastic member stretches in a longitudinal direction, it is possible to stretch the outer members 12F and 12B to a predetermined stretch rate at which the outer members 12F and 12B stretch without wrinkles. As the elastic members 15 to 19, in addition to an elongated elastic member (illustrated example) such as a rubber thread, a known elastic member such as a belt-shaped member, a net-shaped member, or a film-shaped member can be used without particular limitation. As the elastic members 15 to 19, either a synthetic rubber or a natural rubber may be used.

The elastic members 15 to 19 in the illustrated example will be described in more detail. In the waist portion W of the outer members 12F and 12B, a plurality of waist elastic members 17 is attached at intervals in a front-back direction so as to be continuous over the entire width direction WD. One or more waist elastic members 17 disposed in a region adjacent to the under-waist portion U may overlap with the inner member 200, or may be disposed on both sides thereof in the width direction except for the center in the width direction overlapping with the inner member 200. As the waist elastic member 17, it is preferable to dispose 2 to 15 rubber threads, particularly 4 to 10 rubber threads each having a fineness of 155 to 1880 dtex, particularly about 470 to 1240 dtex (in a case of a synthetic rubber, having a cross section of 0.05 to 1.5 mm², particularly about 0.1 to 1.0 mm² in a case of a natural rubber) at intervals of 2 to 12 mm, particularly 3 to 7 mm. A resultant stretch rate of the waist portion W in the width direction WD is preferably 150 to 400%, and particularly preferably about 220 to 320%. In the waist portion W, all of the waist elastic members 17 in the front-back direction LD do not have to have the same fineness and the same stretch rate. For example, the fineness and the stretch rate of the elastic member 17 may be different between an upper portion and a lower portion of the waist portion W.

In the under-waist portion U of the outer members 12F and 12B, a plurality of under-waist elastic members 15 and 19 formed of an elongated elastic member is preferably disposed at intervals in a front-back direction. As the under-waist elastic members 15 and 19, it is preferable to dispose 5 to 30 rubber threads each having a fineness of 155 to 1880 dtex, particularly about 470 to 1240 dtex (in a case of a synthetic rubber, having a cross section of 0.05 to 1.5 mm$^2$, particularly about 0.1 to 1.0 mm$^2$ in a case of a natural rubber) at intervals of 1 to 15 mm, particularly 3 to 8 mm. A resultant stretch rate of the under-waist portion U in the width direction WD is preferably 200 to 350%, and particularly preferably about 240 to 300%.

In the gluteal cover portion C of the back outer member 12B, a cover portion elastic member 16 formed of an elongated elastic member is preferably attached. The gluteal cover portion C is contracted toward the center in the width direction WD by the cover portion elastic member 16. As the cover portion elastic member 16, it is preferable to dispose a rubber thread having a fineness of 155 to 1880 dtex, particularly about 470 to 1240 dtex (in a case of a synthetic rubber, having a cross section of 0.05 to 1.5 mm$^2$, particularly about 0.1 to 1.0 mm$^2$ in a case of a natural rubber). A resultant stretch rate of the gluteal cover portion C in the width direction WD is preferably 150 to 300%, and particularly preferably about 180 to 260%.

Meanwhile, in a case where an inguinal cover portion is disposed in the front outer member 12F, a cover portion elastic member can be disposed similarly to the gluteal cover portion C.

In a case where the elastic members 15, 16, and 19 are disposed in a front-back direction range having the absorber 56 like the under-waist portion U and the gluteal cover portion C in the illustrated example, in order to prevent contraction of the absorber 56 in the width direction WD in a part or the whole thereof, a width direction intermediate portion including a part or the whole of a portion overlapping with the absorber 56 in the width direction WD (preferably including the whole of the inner and outer bonded portions 201 and 202) is a non-stretchable region A1, and both sides thereof in the width direction are stretchable regions A2. The waist portion W is preferably the stretchable region A2 over the entire width direction WD. However, like the under-waist portion U, the waist portion W may have the non-stretchable region A1 in a width direction intermediate portion.

The stretchable region A2 and the non-stretchable region A1 can be formed, in manufacture of the outer members 12F and 12B, by fixing the elastic members 15, 16, and 19 in at least both end portions in a stretchable direction in the stretchable region A2 through a hot melt adhesive without fixing the elastic members 15, 16, and 19 in a region to be the non-stretchable region A1, and cutting the elastic members 15, 16, and 19 at one place in a width direction intermediate portion or cutting the elastic members 15, 16, and 19 finely at many places in the region to be the non-stretchable region A1 by means of pressing and heating of the elastic members 15, 16, and 19 to leave elasticity in the stretchable region A2 and to destroy elasticity in the non-stretchable region A1. In the former case, as illustrated in FIG. 4, in the non-stretchable region A1, a cutting residue continuous from the elastic members 15, 16, and 19 in the stretchable region A2 remains in the outer members 12F and 12B while being contracted to a natural length alone as an unnecessary elastic member 18. In the latter case, although not illustrated, a cutting residue continuous from the elastic members 15, 16, and 19 in the stretchable region A2 and a cut piece of an elastic member not continuous from the elastic members 15, 16, and 19 in either of the stretchable regions A2 remain in the outer bodies 12F and 12B while being contracted to a natural length alone as an unnecessary elastic member.

As illustrated in FIG. 8, the waist portion W of each of the outer members 12F and 12B includes the waist inner sheet layer 121 facing an inside of the waist elastic member 17 and the waist outer sheet layer 122 facing an outside of the waist elastic member 17. The waist elastic member 17 is bonded to the waist inner sheet layer 121 and the waist outer sheet layer 122 via the hot melt adhesive HM.

In the present example, the under-waist portion U of each of the outer members 12F and 12B includes an under-waist inner sheet layer 123 facing insides of the under-waist elastic members 15 and 19 and an under-waist outer sheet layer 124 facing outsides of the under-waist elastic members 15 and 19. The under-waist elastic members 15 and 19 are bonded to the under-waist inner sheet layer 123 and the under-waist outer sheet layer 124 via the hot melt adhesive HM.

Furthermore, in the present example, the gluteal cover portion C of the back outer member 12B includes a cover portion inner sheet layer 125 facing an inside of the cover portion elastic member 16 and a cover portion outer sheet layer 126 facing an outside of the cover portion elastic member 16. The cover portion elastic member 16 is bonded to the cover portion inner sheet layer 125 and the cover portion outer sheet layer 126 via the hot melt adhesive HM.

Characteristically, the waist portion W has a first portion P1 closer to the waist opening WO than an intermediate portion in a front-back direction LD and a second portion P2 opposite thereto. Each of the first portion P1 and the second portion P2 has at least one of the waist elastic members 17. The first portion P1 has an over sheet layer 127 folded back at an edge of the waist opening WO from an outside of the waist outer sheet layer 122 and extending to an inside of the waist inner sheet layer 121. The over sheet layer 127 is formed of a sheet material (first sheet material 12S described later in the illustrated example) having a portion folded back at an edge of the waist opening WO from a position outside the waist elastic member 17 in the second portion P2 and extending to a position inside the waist elastic member 17 in the second portion P2. In the first portion P1, the waist elastic member 17 is not fixed to the sheet material forming the over sheet layer 127. In the second portion P2, the waist elastic member 17 is fixed to the sheet material forming the over sheet layer 127, and the sheet material forming the over sheet layer 127 together with the waist elastic member 17 is contracted in the width direction WD.

For this reason, in the illustrated example, the first sheet material 12S forming the under-waist outer sheet layer 124 and the second sheet material 12H forming the under-waist inner sheet layer 123 both go toward the waist opening WO, and are folded inward at an edge of the waist opening WO through the waist portion W. The portion of the first sheet material 12S folded inward at the edge of the waist opening WO extends to the leg opening LO side more than the waist elastic member 17 closest to the leg opening LO, and the portion of the second sheet material 12H folded inward at the edge of the waist opening WO extends only to a boundary between the first portion P1 and the second portion P2. In the first portion P1, the waist elastic member 17 is bonded to the second sheet material 12H via the hot melt adhesive HM, and the first sheet material 12S is not bonded to the second sheet material 12H. In the second portion P2, the waist elastic member 17 is bonded to the first sheet material 12S facing an inside of the waist elastic member 17 via the hot melt adhesive HM, the waist elastic member 17 is bonded to the second sheet material 12H facing an outside of the waist elastic member 17 via the hot melt adhesive HM, and the first sheet material 12S is bonded to the second sheet material 12H via the hot melt adhesive HM. As a result, the over sheet layer 127 is formed of the first sheet material 12S, the waist outer sheet layer 122 is formed of the second sheet material 12H, and the waist inner sheet layer 121 is formed of the second sheet material 12H in the first portion P1, and is formed of the first sheet material 12S in the second portion P2. In the illustrated example, the cover portion elastic member 16 is disposed. The cover portion outer sheet layer 126 is formed of the first sheet material 12S, and the cover portion inner sheet layer 125 is formed of the second sheet material 12H. As illustrated in FIG. 5, a portion 12r folded inward at the edge of the waist opening WO in the first sheet material 12S is preferably extended so as to cover an end portion of the inner member 200 on the waist opening WO side.

This structure in the illustrated example not only simplifies the configurations of the sheet material 12S and 12H but also can be manufactured easily by sandwiching the under-waist elastic members 15 and 19 between the first sheet material 12S and the second sheet material 12H to bond the first sheet material 12S to the second sheet material 12H and to fix the under-waist elastic members 15 and 19, then folding back the end portions of the first sheet material 12S and the second sheet material 12H, sandwiching the waist elastic member 17 between the folded portions, bonding the first sheet material 12S to the second sheet material 12H, and fixing the waist elastic member 17. In the first portion P1, two sheet layers are required in each of the outside and the inside of the waist elastic member 17, and one sheet layer is only required in each of the outside and the inside of each of the waist under-waist elastic members 15 and 19. Therefore, the structure in the illustrated example is preferable. In contrast to the illustrated example, the portion of the first sheet material 12S folded inward at the edge of the waist opening WO extends only to the boundary between the first portion P1 and the second portion P2, and the portion of the second sheet material 12H folded inward at the edge of the waist opening WO may extend to the leg opening LO side more than the waist elastic member 17 closest to the leg opening LO. Of course, both the portion of the first sheet material 12S folded inward at the edge of the waist opening WO and the portion of the second sheet material 12H folded inward at the edge of the waist opening WO may extend to the leg opening LO side more than the waist elastic member 17 closest to the leg opening LO.

In the outer members 12F and 12B described above, as is apparent from the trace diagrams of a trial product illustrated in FIGS. 11 and 12, the waist inner sheet layer 121 and the waist outer sheet layer 122 are covered with the over sheet layer 127. Therefore, all the waist elastic members 17 included in the first portion P1 including the waist elastic member 17 closest to the waist opening WO touch a skin through the two sheet layers. A portion from an edge of the waist opening WO to the waist elastic members 17 in the first portion P1 is covered with the over sheet layer 127 released from the waist elastic members 17, and a free portion of the over sheet layer 127 can be freely deformed with respect to the waist elastic members 17. Therefore, when the product is held by hand, feel of the waist portion W is soft. In addition, feeling that the over sheet layer 127 slips against the waist inner sheet layer 121 and the waist outer sheet layer 122 is perceived as a smooth hand feel, and the free portion of the over sheet layer 127 is perceived as a soft hand feel. Therefore, a softness characteristic including softness and smoothness which are hardly achieved at the same time is exhibited. Furthermore, in the second portion P2, a contraction force of the waist elastic members 17 directly act on the sheet material 12S forming the over sheet layer 127, and the sheet material 12S has firm contraction wrinkles. In the first portion P1, the sheet material 12S forming the over sheet layer 127 is released from the waist elastic members 17, but has contraction wrinkles continuous from the second portion P2 due to an influence of the contraction deformation of the second portion P2. That is, not only the portion from the edge of the waist opening WO to the waist elastic members 17 of the first portion P1 is covered with the over sheet layer 127 released from the waist elastic member 17, but also contraction wrinkles are formed in at least the first portion P1 of the over sheet layer 127. Due to the contraction wrinkles, a cushioning property of a corner pressed against a skin when the product is held by hand or worn at the time of wearing or purchasing, that is, a cushioning property of a portion including a waist elastic member 17 closest to the waist opening WO increases. Therefore, texture of the end portion of the waist opening WO is better than that of a diaper having a conventional over sheet layer 127. Note that in the trial product illustrated in FIGS. 11 and 12, the number of the waist elastic members 17 is different from that in the example illustrated in FIG. 8.

The position of the boundary between the first portion P1 and the second portion P2 can be determined appropriately. However, in a case where 4 to 10 waist elastic members 17 are disposed at intervals of 3 to 7 mm in the front-back direction LD, when the boundary between the first portion P1 and the second portion P2 is located within a range from a position of a waist elastic member 17 first from the waist opening WO to a position of a waist elastic member 17 fifth from the waist opening WO, improvement of softness by release of the over sheet layer 127 in the first portion P1 and improvement of a cushioning property by formation of contraction wrinkles are easily achieved at the same time, and therefore this is preferable. The position of the boundary between the first portion P1 and the second portion P2 may be different or the same between the front outer member 12F and the back outer member 12B. For example, as in the example illustrated in FIGS. 11 and 12, when the length of the first portion P1 in the front outer member 12F in the front-back direction LD is longer than the length of the first portion P1 in the back outer member 12B in the front-back direction LD, a cushioning property against an abdomen is high. The position of the boundary between the first portion P1 and the second portion P2 may be different or the same between the inside and the outside of the waist portion W. However, as in the example illustrated in FIG. 9, when the boundary between the first portion P1 and the second portion P2 outside the waist portion W is closer to the waist opening WO than the boundary between the first portion P1 and the second portion P2 inside the waist portion W, the appearance of the waist portion W does not give a loose impression at the time of wearing, and therefore this is preferable. Specifically, when the boundary between the first portion P1 and the second portion P2 outside the waist portion W is located within a range from a position of a waist elastic member 17 first from the waist opening WO to a position of a waist elastic member 17 third from the waist opening WO, the boundary between the first portion P1 and the second portion P2 inside the waist portion W is located within a range from a position of a waist elastic member 17 second from the waist opening WO to a position of a waist elastic member 17 fifth from the waist opening WO, and there are one or more (three or less) waist elastic members 17 between the boundary between the first portion P1 and the second portion P2 outside the waist portion W and the boundary between the first portion P1 and the second portion P2 inside the waist portion W, a balance among a neat appearance, a soft hand feel, and comfortable wearing is particularly excellent.

As illustrated in FIG. 9, it is also preferable to secure a wide interval between the edge of the waist opening WO and the waist elastic member 17 closest to the waist opening WO in the front-back direction LD. However, if the interval is too wide, the contraction wrinkles formed in the first portion P1 by contraction of the second portion P2 do not easily reach the edge of the waist opening WO or the vicinity thereof, and a cushioning property of the edge of the waist opening WO may be insufficient. Therefore, this interval is preferably short, and is usually 5 mm or less, and particularly preferably 2 to 4 mm. As a result, the contraction wrinkles formed in the first portion P1 by contraction of the second portion P2 are formed nicely to the edge of the waist opening WO or the vicinity thereof.

In the illustrated example, all the sheet layers of the outer members 12F and 12B including the waist inner sheet layer 121, the waist outer sheet layer 122, and the over sheet layer 127 are formed only by the first sheet material 12S and the second sheet material 12H. However, the number of the sheet materials and structures thereof are not limited to the illustrated example, and can be changed appropriately. For example, in the illustrated example, the waist inner sheet layer 121 and the waist outer sheet layer 122 are formed by folding back a single sheet of the second sheet material 12H, but each of the waist inner sheet layer 121 and the waist outer sheet layer 122 may be formed of a single sheet of sheet material. As illustrated in FIG. 9, all the sheet layers may be formed of a single sheet of sheet material 12U.

As the first sheet material 12S and the second sheet material 12H, any material can be used without particular limitation, but a nonwoven fabric is preferably used. Examples thereof include a nonwoven fabric formed of a synthetic fiber such as an olefin-based fiber including polyethylene and polypropylene, a polyester-based fiber, or a polyamide-based fiber, or a mixed fiber or a composite fiber using two or more kinds of these fibers. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. In a case where a nonwoven fabric is used, the nonwoven fabric preferably has a basis weight of about 10 to 30 g/m² per sheet.

When the first sheet material 12S and the second sheet material 12H are slippery materials, the over sheet layer 127 is slippery with respect to the waist inner sheet layer 121 and the waist outer sheet layer 122, and resistance during deformation of the free portion of the over sheet layer 127 is reduced. Therefore, a surface of the first sheet material 12S facing the second sheet material 12H and a surface of the second sheet material 12H facing the first sheet material 12S preferably each have a nonwoven fabric average surface friction coefficient MIU of 0.30 or less, particularly 0.05 to 0.20 (both machine direction (MD) and cross direction (CD)) based on Kawabata's Evaluation System for Fabrics (KES method), and preferably each have a surface friction coefficient variation deviation MMD of 0.01 or less, particularly 0.003 to 0.008 (both MD and CD). This further improves softness of a portion having the over sheet layer 127. The MIU and MMD can be measured with a friction tester KES-SE manufactured by Kato Tech Co., Ltd.

An elastic member is fixed to the outer members 12F and 12B with the hot melt adhesive HM by various application methods. In a portion having the elastic members 15 to 19, a pair of facing sheet layers, that is, the waist inner sheet layer 121 and the waist outer sheet layer 122 or the under-waist inner sheet layer 123 and the under-waist outer sheet layer 124 are preferably bonded to each other with the hot melt adhesive HM for fixing the elastic members 15 to 19. In a portion having no elastic members 15 to 19, a pair of facing sheet layers may be bonded to each other with the hot melt adhesive HM or by material welding such as heat sealing or ultrasonic sealing, and a part or the whole of a pair of the facing sheet layers does not have to be bonded. In a portion having the elastic members 15 to 19 in the outer members 12F and 12B in the illustrated example, by applying the hot melt adhesive HM only to outer peripheral surfaces of the elastic members 15 to 19 by an application means such as a comb gun or a SureWrap nozzle, and sandwiching the elastic members 15 to 19 between the waist inner sheet layer 121 and the waist outer sheet layer 122, the elastic members 15 to 19 are fixed to the waist inner sheet layer 121 and the waist outer sheet layer 122 only with the hot melt adhesive HM applied to the outer peripheral surfaces of the elastic members 15 to 19, and both the sheet layers are fixed to each other. The elastic members 15 to 19 may be fixed to both the sheet layers only at both end portions in a stretchable direction in the stretchable region A2.

Cover Nonwoven Fabric

In an outer member separated type underpants-type disposable diaper, the inner member 200 is exposed between the front outer member 12F and the back outer member 12B. Therefore, in order to prevent the liquid impervious sheet 11 from being exposed to a back surface of the inner member 200, the outer member separated type underpants-type disposable diaper preferably includes a cover nonwoven fabric 13 covering the back surface of the inner member 200 from a portion between the front outer member 12F and the inner member 200 to a portion between the back outer member 12B and the inner member 200.

As a nonwoven fabric used for the cover nonwoven fabric 13, for example, a material similar to those of the outer members 12F and 12B can be appropriately selected, and the nonwoven fabric used for the cover nonwoven fabric 13 is not particularly limited by the type of a fiber or a method for bonding (interlacing) fibers. However, it is desirable to use an air through nonwoven fabric. In this case, the basis weight is preferably 20 to 40 g/m² and the thickness is preferably 0.3 to 1.0 mm. As the cover nonwoven fabric 13, an imperforated nonwoven fabric having no hole passing therethrough from the front to the back or a perforated nonwoven fabric having many holes passing therethrough from the front to the back at intervals may be used.

The front-back direction range of the cover nonwoven fabric 13 is not particularly limited, and as illustrated in FIGS. 2 and 5, may extend in the front-back direction LD over the entire region from a front end to a back end of the inner member 200. As illustrated in FIG. 7, the front-back direction range of the cover nonwoven fabric 13 may extend in the front-back direction LD from a front-back direction intermediate position of a region where the front outer member 12F and the inner member 200 overlap with each other to a front-back direction intermediate position of a region where the back outer member 12B and the inner member 200 overlap with each other. In the case of the example illustrated in FIG. 7, a front-back direction length 13y of an overlapping portion between the cover nonwoven fabric 13 and the front outer member 12F and a front-back direction length 13y of an overlapping portion between the cover nonwoven fabric 13 and the back outer member 12B can be appropriately determined, but can be each about 20 to 40 mm in a usual case.

The width direction range of the cover nonwoven fabric 13 is a range in which a back surface exposed portion of the liquid impervious sheet 11 can be concealed. For this reason, in the illustrated example, the liquid impervious sheet 11 is exposed between base ends of the left and right side gathers 60. Therefore, the cover nonwoven fabric 13 is disposed so as to cover a width direction range from a back surface side of a base portion of at least one of the side gathers 60 to a back surface side of a base portion of the other of the side gathers 60. This makes it possible to conceal the liquid impervious sheet 11 with the cover nonwoven fabric 13 and the gather nonwoven fabric 62 of the side gather 60. In addition, not by covering a back surface side of the base portion of the side gather 60 with width direction both end portions of the cover nonwoven fabric 13 but by covering a back surface side of the width direction both end portions of the cover nonwoven fabric 13 with the gather nonwoven fabric 62, it is possible to conceal the liquid impervious sheet 11 with the cover nonwoven fabric 13 and the gather nonwoven fabric 62. In this case, since both sides of the cover nonwoven fabric 13 are covered with the gather nonwoven fabric 62, both sides of the cover nonwoven fabric 13 are less likely to be peeled off from the liquid impervious sheet 11 advantageously.

The inner surface and the outer surface of the cover nonwoven fabric 13 can be bonded to facing surfaces thereof via a hot melt adhesive. As a fixing region of the cover nonwoven fabric 13, the entire front-back direction and the entire width direction of the cover nonwoven fabric 13 can be fixed, or a part thereof can be non-fixed. For example, when width direction both end portions of the cover nonwoven fabric 13 are non-fixed, even if a side of the absorber 56 is contracted somewhat due to an influence of the side gather 60, the influence is small, and wrinkles or creases are less likely to be formed in the cover nonwoven fabric 13 advantageously. In this case, the widths of the non-fixed portions at width direction both end portions of the cover nonwoven fabric 13 may be determined appropriately, but can be, for example, 3 to 10 mm, preferably 5 to 8 mm.

Inner and Outer Bonded Portion

The inner member 200 can be fixed to the outer members 12F and 12B by a bonding means by material welding such as heat sealing or ultrasonic sealing, or with a hot melt adhesive. In the illustrated example, via a hot melt adhesive applied to the back surface of the inner member 200, that is, the back surface of the liquid impervious sheet 11 and the root portion 65 of the side gather 60 in this case, the inner member 200 is fixed to the inner surfaces of the outer members 12F and 12B. The inner and outer bonded portions 201 and 202 for fixing the inner member 200 to the outer members 12F and 12B can be disposed in almost the entire region where the inner member 200 overlaps with the outer members 12F and 12B as illustrated in FIG. 2, and can be disposed, for example, in a portion excluding width direction both end portions of the inner member 200.

Explanation of Terms in Specification

The following terms in the specification have the following meanings unless otherwise specified in the specification.

"Front-back (longitudinal) direction" means a direction connecting a ventral side (front side) and a dorsal side (back side), and "width direction" means a direction orthogonal to the front-back direction (left-right direction).

"Front surface side" means a side closer to a wearer's skin when an underpants-type disposable diaper is worn. "Back surface side" means a side far from a wearer's skin when an underpants-type disposable diaper is worn.

"Front surface" means a surface of a member closer to a wearer's skin when an underpants-type disposable diaper is worn. "Back surface" means a surface far from a wearer's skin when an underpants-type disposable diaper is worn.

"Stretch rate" means a value obtained when a natural length is assumed to be 100%.

"Gel strength" is measured as follows. To 49.0 g of artificial urine (mixture of 2% by weight of urea, 0.8% by weight of sodium chloride, 0.03% by weight of calcium chloride dihydrate, 0.08% by weight of magnesium sulfate heptahydrate, and 97.09% by weight of deionized water), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Incidentally, fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 100 to calculate the weight per square meter to be used as a basis weight.

"Thickness" is automatically measured under conditions that a load is 0.098 N/cm$^2$ and a pressing area is 2 cm$^2$ using an automatic thickness meter (KES-G5 handy compression measuring program).

Water absorption capacity is measured in accordance with JIS K7223-1996 "Test method for water absorption capacity of super absorbent polymer".

Water absorption rate is "time to end point" when JIS K7224-1996 "Test method for water absorption rate of super absorbent polymer" is performed using 2 g of super absorbent polymer and 50 g of physiological saline.

"Unfolded state" means a flatly unfolded state without contraction or slackness.

The size of each portion means a size not in a natural length state but in an unfolded state unless otherwise specified.

In a case where environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention is applicable to an underpants-type disposable diaper.

REFERENCE SIGNS LIST

11 Liquid impervious sheet
12A Side seal portion
12B Back outer member
12E Waist extended portion
12F Front outer member
12F, 12B Outer member
12H Second sheet material
12S First sheet material
13 Cover nonwoven fabric
15, 19 Under-waist elastic member
16 Cover portion elastic member
17 Waist elastic member
18 Unnecessary elastic member
200 Inner member
201, 202 Inner and outer bonded portion
30 Top sheet
40 Intermediate sheet
50 Absorbent element
56 Absorber
58 Wrapping sheet
60 Side gather
60A Tip side portion
60B Root side portion
62 Gather nonwoven fabric
67 Fallen portion
68 Free portion
A1 Non-stretchable region
A2 Stretchable region
C Gluteal cover portion
L Intermediate region
LD Front-back direction
T Lower torso region
U Under-waist portion
W Waist portion
WD Width direction
WO Waist opening
LO Leg opening
121 Waist inner sheet layer
122 Waist outer sheet layer
124 Under-waist outer sheet layer
123 Under-waist inner sheet layer
125 Cover portion inner sheet layer
126 Cover portion outer sheet layer
127 Over sheet layer
P1 First portion
P2 Second portion
HM Hot melt adhesive

The invention claimed is:

1. An underpants-type disposable diaper comprising:
an outer member forming a lower torso portion over a front body and a back body;
an inner member attached to the outer member so as to extend from the front body to the back body and including an absorber;
a waist opening; and
a pair of left and right leg openings,
a waist portion of the outer member including: a plurality of elongated waist elastic members disposed in a width direction at intervals; a waist inner sheet layer facing insides of the waist elastic members; and a waist outer sheet layer facing outsides of the waist elastic members,
the waist elastic members being bonded to at least one of the waist inner sheet layer and the waist outer sheet layer via a hot melt adhesive on the side of the waist outer sheet layer that faces the waist inner sheet layer, wherein
the waist portion has a first portion and a second portion, the first portion is a portion of the waist portion located closer to the waist opening than a middle of the waist portion in a front-back direction, and the second portion is a portion of the waist portion different from the first portion, and
the first portion and the second portion each have at least one of the waist elastic members, the first portion includes an over sheet layer folded back at an edge of the waist opening from an outside of the waist outer sheet layer and extending to an inside of the waist inner sheet layer,
the over sheet layer is formed of a sheet material having a portion folded back at the edge of the waist opening from a position outside the at least one of the waist elastic members in the second portion and extending to a position inside the at least one of the waist elastic members in the second portion,
the first portion is a portion wherein the sheet material of the over sheet layer is not bonded to either the waist inner sheet layer or the waist outer sheet layer, and
in the second portion, the at least one of the waist elastic members is directly bonded to the sheet material of the over sheet layer, and the sheet material of the over sheet layer is contracted in a width direction together with the at least one of the waist elastic members.

2. The underpants-type disposable diaper according to claim 1, wherein
the outer member has an under-waist portion located below the waist portion at the lower torso portion,
the under-waist portion of the outer member includes: a plurality of elongated under-waist elastic members disposed in a width direction at intervals; an under-waist inner sheet layer facing insides of the under-waist elastic members; and an under-waist outer sheet layer facing outsides of the under-waist elastic members,
the under-waist elastic members are bonded to the under-waist inner sheet layer and the under-waist outer sheet layer via a hot melt adhesive,
a first sheet material forming the under-waist outer sheet layer and a second sheet material forming the under-waist inner sheet layer both pass through the waist portion and are folded inward at the edge of the waist opening,
the portion folded inward at the edge of the waist opening in the first sheet material extends to a leg opening side more than a waist elastic member closest to the leg opening,
the portion folded inward at the edge of the waist opening in the second sheet material extends only to a boundary between the first portion and the second portion,
the over sheet layer is formed of the first sheet material, the waist outer sheet layer is formed of the second sheet material, the waist inner sheet layer is formed of the second sheet material in the first portion, and is formed of the first sheet material in the second portion, in the first portion, the waist elastic members are bonded to the second sheet material via a hot melt adhesive, and the first sheet material is not bonded to the second sheet material, and in the second portion, the waist elastic members are bonded to the first sheet material facing insides of the waist elastic members via a hot melt adhesive, the waist elastic members are bonded to the second sheet material facing outsides of the waist elastic members via a hot melt adhesive, and the first sheet material is bonded to the second sheet material via a hot melt adhesive.

3. The underpants-type disposable diaper according to claim 2, wherein four to ten of the waist elastic members are disposed at intervals of 3 to 7 mm in the front-back direction, and the boundary between the first portion and the second portion is located in a range from a position of a first waist elastic member from the waist opening to a position of a fifth waist elastic member from the waist opening.

4. The underpants-type disposable diaper according to claim 2, wherein an interval between the edge of the waist opening and the waist elastic member closest to the waist opening in the front-back direction is 5 mm or less.

5. The underpants-type disposable diaper according to claim 2, wherein a surface of the first sheet material facing the second sheet material and a surface of the second sheet material facing the first sheet material each have an average surface friction coefficient MIU of 0.30 or less.

6. The underpants-type disposable diaper according to claim 1, wherein a boundary between the first portion and the second portion outside the waist portion is closer to the waist opening than a boundary between the first portion and the second portion inside the waist portion.

7. The underpants-type disposable diaper according to claim 3, wherein an interval between the edge of the waist opening and the waist elastic member closest to the waist opening in the front-back direction is 5 mm or less.

8. The underpants-type disposable diaper according to claim 3, wherein a surface of the first sheet material facing the second sheet material and a surface of the second sheet material facing the first sheet material each have an average surface friction coefficient MIU of 0.30 or less.

9. The underpants-type disposable diaper according to claim 4, wherein a surface of the first sheet material facing the second sheet material and a surface of the second sheet material facing the first sheet material each have an average surface friction coefficient MIU of 0.30 or less.

10. The underpants-type disposable diaper according to claim 2, wherein a boundary between the first portion and the second portion outside the waist portion is closer to the waist opening than a boundary between the first portion and the second portion inside the waist portion.

11. The underpants-type disposable diaper according to claim 3, wherein a boundary between the first portion and the second portion outside the waist portion is closer to the waist opening than a boundary between the first portion and the second portion inside the waist portion.

12. The underpants-type disposable diaper according to claim 4, wherein a boundary between the first portion and the second portion outside the waist portion is closer to the waist opening than a boundary between the first portion and the second portion inside the waist portion.

13. The underpants-type disposable diaper according to claim 5, wherein a boundary between the first portion and the second portion outside the waist portion is closer to the waist opening than a boundary between the first portion and the second portion inside the waist portion.

* * * * *